US008697751B2

(12) United States Patent
Sakai et al.

(10) Patent No.: US 8,697,751 B2
(45) Date of Patent: Apr. 15, 2014

(54) PHARMACEUTICAL COMPOSITION CONTAINING PROSTAGLANDIN

(75) Inventors: Yusuke Sakai, Hyogo (JP); Akira Ohtori, Hyogo (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/206,784

(22) Filed: Aug. 10, 2011

(65) Prior Publication Data

US 2011/0294880 A1 Dec. 1, 2011

Related U.S. Application Data

(63) Continuation of application No. 10/573,191, filed as application No. PCT/JP2004/015828 on Oct. 26, 2004, now abandoned.

(30) Foreign Application Priority Data

Nov. 7, 2003 (JP) ................................ 2003-378196

(51) Int. Cl.
*A61K 31/557* (2006.01)
(52) U.S. Cl.
USPC .......................................... 514/573; 549/422
(58) Field of Classification Search
None
See application file for complete search history.

(56) References Cited

U.S. PATENT DOCUMENTS

| | | | |
|---|---|---|---|
| 4,191,772 A | 3/1980 | Woog et al. | |
| 4,839,371 A | 6/1989 | Kruse et al. | |
| 5,192,535 A | 3/1993 | Davis et al. | |
| 5,296,504 A | 3/1994 | Stjernschantz et al. | |
| 5,352,708 A | 10/1994 | Woodward et al. | |
| 5,510,383 A | 4/1996 | Bishop et al. | |
| 5,631,287 A | 5/1997 | Schneider | |
| 5,767,135 A | 6/1998 | Fernandez-Pol | |
| 5,767,153 A | 6/1998 | Bowman et al. | |
| 6,342,524 B1 | 1/2002 | Hellberg et al. | |
| 6,635,654 B1 | 10/2003 | Chang et al. | |

FOREIGN PATENT DOCUMENTS

| | | |
|---|---|---|
| EP | 0289349 | 11/1988 |
| EP | 0330511 | 8/1989 |
| EP | 0639563 | 2/1995 |
| EP | 0831775 | 4/1998 |
| EP | 1321144 | 6/2003 |
| JP | 53121920 | 10/1978 |
| JP | 60051105 | 3/1985 |
| JP | 01221317 | 9/1989 |
| JP | 02000108 | 1/1990 |
| JP | 03501025 | 3/1991 |
| JP | 07010833 | 1/1995 |
| JP | 08501310 | 2/1996 |
| JP | 10182465 | 7/1998 |
| JP | 11500122 | 1/1999 |
| JP | 2001010958 | 1/2001 |
| JP | 2002161037 | 6/2002 |
| WO | WO-9002553 | 3/1990 |
| WO | WO-9406433 | 3/1994 |
| WO | WO-9640051 | 12/1996 |
| WO | WO-9729752 | 8/1997 |

OTHER PUBLICATIONS

"Crospovidone; Povidone", European Pharmacopoeia, Sixth edition, vol. 2, (2007), 1628-1629; 2732-2734.
"Goodman & Gilman's The Phamacological Basis of Therapeutics", 10th edition, McGraw-Hill, (2001), pp. 5 & 8.
"Material Safety Data Sheet", [online Jul. 22, 2010], 15(R)-17-phenyl trinor Prostaglandin F2.alpha.isopropyl ester, Product and Company identification, Synonyms, Retrieved from URL:<http://www.caymanchem.com/msdss/16828m.pdf.
"Prostaglandin F2å isopropyl ester", (Dinoprost) Cayman Chemical Item No. 16030; http://www.caymanchem.com/app/template/Product.vm/catalog/16030, (Dec. 15, 2010).
BASF, "Cremophor® EL", Technical leaflet, (Jul. 1997), 7 pages.
Ibrahim, N. K., et al., "Phase I and pharmacokinetic study of ABI-007, a cremophor-free, protein-stabilized, nanoparticle formulation of paclitaxel", Clin Cancer Res, 8, (May 1, 2002), 1038-1044.
Merck & Co., Inc., "7783. Povidone; Crospovidone", The Merck Index: An encyclopedia of chemicals, drugs, and biologicals, 13th Edition, (2001), 1374.
Okano, "Introduction to Modern Pharmaceutics", lines 6-9, Nankodo Co., Ltd., (Apr. 10, 1987), 262.
Senju Pharmaceutical Co., Ltd., Non final office action mailed Oct. 5, 2009 for U.S. Appl. No. 10/573,191.
Senju Pharmaceutical Co., Ltd., Non-final Office Action mailed Mar. 30, 2011 for U.S. Appl. No. 10/573,191.
Senju Pharmaceutical Co., Ltd., PCT International Search Report mailed Jan. 25, 2005 for PCT/JP2004/015828.

*Primary Examiner* — Lezah Roberts
*Assistant Examiner* — Nannette Holloman
(74) *Attorney, Agent, or Firm* — Wenderoth, Lind & Ponack, L.L.P.

(57) ABSTRACT

An object of the present invention is to provide a stable aqueous pharmaceutical composition which suppresses degradation of prostaglandin $F_{2\alpha}$ in a preparation containing prostaglandin $F_{2\alpha}$. The object was attained by formulating a prostaglandin $F_{2\alpha}$ derivative into an oil-in-water emulsion together with an oil, for example, medium chain fatty acid triglyceride, a water-soluble polymer and water.

6 Claims, No Drawings

PHARMACEUTICAL COMPOSITION CONTAINING PROSTAGLANDIN

CROSS-REFERENCE to RELATED APPLICATIONS

The application is a continuation of co-pending U.S. patent application Ser. No. 10/573, 191, filed Sep. 11 , 2007, which is a 371 National Stage Application of International Application No. PCT/JP2004/015828, filed Oct. 26, 2004.

TECHNICAL FIELD

The present invention relates to a pharmaceutical composition which is an oil-in-water emulsion comprising a prostaglandin $F_{2\alpha}$ derivative, an oil, a water-soluble polymer and water, as well as a method of suppressing degradation of prostaglandin $F_{2\alpha}$ in the composition.

BACKGROUND ART

Prostaglandin is a physiologically active substance derived from a polyunsaturated fatty acid, and has various important pharmacological and physiological actions at a very small amount, and therefore, various derivatives thereof have been synthesized and developed for medicine. For example, derivatives of prostaglandin $F_{2\alpha}$ are useful as a medicament for treating glaucoma or ocular hypertension, and some eye drops have already been developed and marketed. However, in order to prepare an aqueous preparation of a derivative of prostaglandin, we should overcome some problems that prostaglandin and a derivative thereof are poorly soluble m water and, when dissolved in water, they are easily degraded, and further a content of prostaglandin and its derivative is reduced due to adsorption onto a container.

So far, as an aqueous liquid preparation of prostaglandin or a derivative thereof, for example, a composition obtained by solubilizing and stabilizing prostaglandin by formation of a complex with etherized cyclodextrin (see Patent Document 1), a fat emulsion of a stable $PGE_1$ analogue (see Patent Document 2), a prostaglandin composition containing a polyethoxylated castor oil (see Patent Document 3), a prostaglandin fat emulsion containing an purified olive oil, phospholipid and water, which can be intravenously administered (see Patent Document 4), and an eye drop containing a prostaglandin derivative in which a nonionic surfactant and/or an antioxidant is blended (see Patent Document 5) are disclosed.

Patent Document 1: Japanese Patent Application Laid-Open (JP-A) No. H01-221317 (corresponding to EP330511)
Patent Document 2: JP-A No. H07-10833
Patent Document 3: JP-A No. H11-500122 (corresponding to WO97/029752)
Patent Document 4: JP-A No. 2001-10958
Patent Document 5: JP-A No. 2002-161037 (corresponding to EP1321144)

DISCLOSURE OF THE INVENTION

An object of the present invention is to provide a new aqueous pharmaceutical composition in which degradation of a prostaglandin $F_{2\alpha}$ derivative is suppressed.

Means For Solving Problems

The present inventors have studied to seek a dosage form which can prevent degradation of a prostaglandin $F_{2\alpha}$ derivative in an aqueous pharmaceutical composition containing a prostaglandin $F_{2\alpha}$ derivative. As a result, they have found out that an oil-in-water emulsion obtained by blending an oil, inter alia, medium chain fatty acid triglyceride and a water-soluble polymer can provide a pharmaceutical composition in which degradation of a prostaglandin $F_{2\alpha}$ derivative is remarkably suppressed, and have completed the present invention.

That is, the present invention provides the following inventions:

(1) a pharmaceutical composition comprising an oil-in-water emulsion containing a. prostaglandin $F_{2\alpha}$ derivative, an oil, a water-soluble polymer and water,
(2) the pharmaceutical composition according to (1), wherein the prostaglandin $F_{2\alpha}$ derivative is at least one member selected from latanoprost, isopropyl unoprostone, travoprost and bimatoprost,
(3) the pharmaceutical composition according to (2), wherein the prostaglandin $F_{2\alpha}$ derivative is latanoprost,
(4) the pharmaceutical composition according to (1), wherein the water-soluble polymer is at least one member selected from a polyvinyl compound, a water-soluble cellulose compound and a polysaccharide,
(5) the pharmaceutical composition according to (4), wherein the polyvinyl compound is polyvinyl alcohol,
(6) the pharmaceutical composition according to (1), wherein the oil is an animal or vegetable oil and/or medium chain fatty acid triglyceride,
(7) the pharmaceutical composition according to (6), wherein the medium chain fatty acid triglyceride is Miglyol,
(8) the pharmaceutical composition according to any one of (1) to (7), wherein the pharmaceutical composition is an ophthalmological composition,
(9) the pharmaceutical composition according to (8), wherein the ophthalmological composition is an eye drop,
(10) an eye drop which is an oil-in-water emulsion, comprising latanoprost, Miglyol, polyvinyl alcohol and water,
(11) a method of suppressing degradation of a prostaglandin $F_{2\alpha}$ derivative in an emulsion, comprising blending a prostaglandin $F_{2\alpha}$ derivative, an oil, a water-soluble polymer and water to form an oil-in-water emulsion, and
(12) a method of suppressing degradation of latanoprost in an emulsion, comprising blending latanoprost, miglyol, polyvinyl alcohol and water to form an oil-in-water emulsion.

Effect Of The Invention

According to the present invention, degradation of prostaglandin $F_{2\alpha}$ can be remarkably suppressed. Therefore, a stable pharmaceutical composition incorporating prostaglandin $F_{2\alpha}$ can be prepared, and subjected to use.

Best Mode For Carrying Out The Invention

The present invention will be explained in more detail.
The pharmaceutical composition of the present invention is an oil-in-water emulsion containing an oil, a water-soluble polymer and water together with a prostaglandin $F_{2\alpha}$ derivative. By adopting such a dosage form, degradation of a prostaglandin $F_{2\alpha}$ derivative can be remarkably suppressed.

Prostaglandin $F_{2\alpha}$ derivative used in the present invention includes a pharmaceutically acceptable salt and ester thereof. Examples of the pharmaceutically acceptable salt include salts with an organic base e.g. an alkali metal such as sodium and potassium, an alkaline earth metal such as calcium and magnesium, and an ammonium salt, and salts with an inorganic acid such as hydrochloric acid and phosphoric acid, and an organic acid such as acetic acid, citric acid, and succinic acid. Examples of the pharmaceutically acceptable ester include esters of lower alkyl such as methyl, ethyl, propyl, isopropyl, butyl, isobutyl, t-butyl, pentyl and hexyl.

Examples of the prostaglandin $F_{2\alpha}$ derivative to be blended in the pharmaceutical composition of the present invention include latanoprost, isopropyl unoprostone, travoprost, and bimatoprost, and compounds described in JP-A No. 2002-161037 (aforementioned Patent Document 5) and, inter alia, latanoprost is preferable. The prostaglandin $F_{2\alpha}$ derivative can be blended in the pharmaceutical composition of the present invention at a lower limit of about 0.0001 (W/V) %. preferably about 0.001 (W/V) %, and an upper limit of about 0.4 (W/V) %, preferably about 0.05 (W/V) %.

The oil used in the present invention is not particularly limited, but medium chain fatty acid triglyceride, or an animal oil or vegetable oil containing fatty acid triglyceride as a main component, or both of them may be used. Among them, medium chain fatty acid triglyceride is more preferable. Medium chain fatty acid triglyceride refers to saturated fatty acid triglyceride of the carbon number of 4 to 12, or a mixture thereof a majority of which consists of fatty acid triglyceride having such carbon numbers. Practically, a product containing fatty acid triglyceride of the carbon number of 8 (caprylic acid) or 10 (capric acid) as a main component, obtained by hydrolyzing a palm oil, or a palm kernel oil once, purifying, and combining again can be used. Examples of the products (trade names) include Miglyol (Mitsuba Boeki), Coconade (Kao), ODO (Nisshin Oillio), Panasate (Nippon Oil & Fats Co., Ltd.), TCG-M (Higher Alcohol Industry), and Actor (Riken Vitamin) and, inter alia, Miglyol is preferable. Among Miglyol, Miglyol 812 and 810 are particularly preferable. Examples of the animal or vegetable oil include a castor oil, a soybean oil, a peanut oil, a cottonseed oil, an olive oil, a sesame oil, a camellia oil, a sunflower oil, a coconut oil, a palm oil, a palm kernel oil, a peanut oil, a tung oil, a rape seed oil, a corn oil, beef tallow, and lard containing triglyceride of fatty acid having the car lion number of 4 to 24 such as butyric acid, caproic acid, caprylic acid, capric acid, lauric acid, myristic acid, palmitic acid, stearic acid, arachie acid, behenic acid, lignoeeric acid, palmitoleic acid, oleic acid, linoleic acid, linolenic acid, and ricinoleic acid. These oils can be used alone, or in combination with two or more appropriately.

An amount of the oil to be blended in the pharmaceutical composition of the present invention may be appropriately determined depending on an amount of a prostaglandin $F_{2\alpha}$ derivative as far as an oil-in-water emulsion is formed, and a lower limit is about 0.005 W/V %, preferably about 0.1 W/V %, and an upper limit is about 20 W/V %, preferably about 5 W/V %.

In the pharmaceutical composition of the present invention, a water-soluble polymer is used as an emulsifier. In addition to this water-soluble polymer, as an emulsifier, the composition may be appropriately used by combining with phospholipid such as yolk lecithin, or a surfactant.

Water-solubility in the water-soluble polymer means that 1 g or more of the polymer compound can be dissolver in 100 g of water at 20° C. Examples of the water-soluble polymer include water-soluble cellulose compounds such as methylcellulose, hydroxyethylcellulose, hydroxypropylmethyl-cellulose and sodium cellulose, polyvinyl compounds such as polyvinyl alcohol, and polyvinylpyrrolidone, and polysaccharides such as alginic acid, xanthan gum, carrageenan, and chitosan, preferably polyvinyl alcohol and hydroxypropylmethylcellulose, most preferably polyvinyl alcohol. As the polyvinyl alcohol, both of a partially saponified entity and a completely saponified entity can be used. These water-soluble polymer compounds can be used alone, or in combination with two or more of them appropriately.

An amount of the water-soluble polymer to be blended in the pharmaceutical composition of the present invention may be appropriately determined depending on an amount of the oil to be blended as far as an oil-in-water emulsion is formed, and a lower limit is about 0.001 (W/V) %, preferably about 0.1 (W/V) %, and an upper limit is about 20 (W/V) %, preferably about 5 (W/V) %.

Further, various additives such as buffers, isotonics, preservatives, solubilizers, stabilizers, chelating agents, thickeners, and pH adjusting agents may be appropriately blended in the pharmaceutical composition of the present, invention.

Examples of buffers include boric acid or a salt thereof (borax etc.), citric acid or a salt thereof (sodium citrate etc.), tartaric acid or a salt thereof (sodium tartrate etc.), gluconic acid or a salt thereof (sodium gluconate etc.), acetic acid or a salt thereof (sodium acetate etc.), phosphoric or a salt thereof (sodium monohydrogen phosphate, sodium dihydrogen phosphate etc.), various amino acids such as glutamic acid and epsilonaminocaproic acid, and Tris buffers, and a combination thereof.

Examples of the isotonics include sorbitol, glucose, mannitol, glycerin, propylene glycol, sodium chloride, and potassium chloride.

Examples of the preservatives include p-oxybenzoic acid esters, benzalkonium chloride, benzethonium chloride, benzyl alcohol, sorbic acid or a salt thereof, chlorhexidine gluconate, sodium dehydroacetate, cetylpyridimum chloride, alkyldiaminoethylglycine hydrochloride, and chlorobutanol.

Examples of the solubilizers include polyvinylpyrrolidone, polyethylene glycol, propylene glycol, polyoxyethylene hydrogenated castor oil 60, and stearic acid polyoxyl 40.

Examples of the stabilizers include sodium edetate, sodium thiosulfate, ascorbic acid, cyclodextrin, condensed phosphoric acid or a salt thereof, sulfite, citric acid or a salt thereof, and dibutylhydroxytoluene, and the like.

Examples of the chelating agents include sodium edetate, sodium citrate, and condensed phosphoric acid or a salt thereof (sodium condensed phosphate), and the like.

Examples of the thickeners include methylcellulose, hydroxyethylcellulose, hydroxypropylcellulose, hydroxypropylmethylcellulose, sodium chondroitin sulfate, sodium carboxymethylcellulose, polyvinylpyrrolidone, polyvinyl alcohol, and polyethylene glycol, etc.

Examples of the pH adjusting agents include sodium hydroxide, potassium hydroxide, sodium carbonate, sodium bicarbonate, boric acid or a salt thereof (borax), hydrochloric acid, citric acid or a salt thereof (sodium citrate, sodium dihydrogen citrate etc.), phosphoric acid or a salt thereof (disodium hydrogen phosphate, potassium dihydrogen phosphate etc.), acetic acid or a salt thereof (sodium acetate, ammonium acetate etc.), and tartaric acid or a salt thereof (sodium tartrate etc.), and the like.

A median diameter of oil particles of the pharmaceutical composition of the present invention is preferable 0.0001 to 5 μm, more preferably 0.001 to 1 μm, particularly preferably 0.01 to 1 μm. A median diameter can be measured using a particle size distribution measuring apparatus.

A pH of the pharmaceutical composition of the present invention is adjusted to 3 to 10, preferably 5 to 8.

The pharmaceutical composition of the present invention can be systemically administered in an injectable dosage form and also, can be used as an ophthalmological composition such as an eye drop which is locally administered. Since degradation of a prostaglandin $F_{2\alpha}$ derivative is remarkably suppressed, the pharmaceutical composition of the present invention is useful, particularly, for an eye drop which is usually continued to be used for a certain period of term after breaking the seal.

The prostaglandin $F_{2\alpha}$ derivative-containing pharmaceutical composition of the present invention can be provided by a conventional method for preparing an oil-in-water emulsion. As a preferable method, the following can be exemplified. That is, the composition is prepared by adding an emulsifier and, if necessary, the aforementioned additives to water, adding an oil in which a prostaglandin $F_{2\alpha}$ derivative is dissolved to obtain an emulsion, and adjusting a pH to 3 to 10 using a pH adjusting agent. For performing emulsification uniformly, the publicly known means such as a mixer, a homogenizer, a homomixer, a microfluidizer, and a high-pressure homogenizer can be used.

EXAMPLES

The present inventions will be explained more specifically below by way of Test Examples and Preparation Examples, but these are merely exemplary, and the present inventions are not limited by them.

Test Example 1

Stability of Latanoprost in Oil

Test method

As oils, an olive oil, a cottonseed oil, a peanut oil, a rapeseed oil, a soybean oil, a tung oil and Miglyol 812 were used. Five milligram of latanoprost (isopropyl-(Z)-7-[(1R,2R,3R,5S)-3,5-dihydroxy-2-[(3R)-3-hydroxy-5-phenylpentyl]cyclopentyl]-5-hepta noate) was weighed, and each 1000 mg of each oil was added to latanoprost. The mixture was stirred for 30 minutes with a magnetic stirrer so that latanoprost was dissolved to prepare about, 1000 mg of a latanoprost oil solution (5 mg/g). After dissolution was observed with naked eyes, a latanoprost oil solution was sampled, and a latanoprost content was measured by a HPLC method (day 0). Each 500 μL of these latanoprost oil solutions was dispensed in a glass sample bottle, and was stored at 60° C. or 80° C. for 7 days. On seventh day, sampling was performed, a latanoprost content was measured, and a remaining rate was calculated from a ratio relative to a value measured on 0 day. Each sampling was performed by weighing a constant amount of a latanoprost oil solution, and diluted with tetrahydrofuran and the following mobile phase A, and was supplied for measurement of HPLC.

HPLC analysis conditions: a Waters Extera $RP_{18}$, 5 μm, φ4.6×150 mm column was used. As a mobile phase A, a mixture of acetonitrile: 10 mM sodium 1-octanesulfonate aqueous solution (pH 3.5)=35:65 was used, and as a mobile phase B, a mixture of acetonitrile: 10 mM sodium 1-octanesulfonate aqueous solution (pH 3.5)=10:90 was used. A volume of injection was 50 μL and, a ultraviolet spectrophotometer (measuring wavelength: 210 nm) was used as a detector. A column temperature was kept at around 25° C. Analysis was performed by flowing the mobile phase A for 30 minutes and, thereafter, flowing the mobile phase B for 5 minutes for column washing, and the mobile phase A for 7 minutes for equilibration. A flow rate of the mobile phase was 1.5 mL/min.

Test Results

A latanoprost remaining rate (%) in ach oil is shown in Table 1.

TABLE 1

| Latanoprost remaining rate (%) in oil | | |
|---|---|---|
| | 7 days | |
| | 60° C. | 80° C. |
| Olive oil | 103.6 | 78.4 |
| Cottonseed oil | 105.9 | 67.3 |
| Peanut oil | 103.9 | 90.2 |
| Rapeseed oil | 104.2 | 70.5 |
| Soybean oil | 111.1 | 82.4 |
| Tung oil | 93.3 | 42.7 |
| Miglyol 812 | 105.5 | 104.4 |

Apparent from these test results, latanoprost dissolved in the oil was stable at 60° C. in most of oils although it was warmed. At 80° C., latanoprost was particularly stable in Miglyol 812.

Test Example 2

Stability of Latanoprost-Containing Oil-in-Water Emulsion

Test method

Into the mixture of 0.01 of latanoprost, 2.0 g of Miglyol 812, 4.0 g of Gosenol EGOS (Trade name, partially saponified polyvinyl alcohol, The Nippon Synthetic Chemical Industry Co., Ltd.), 5.2 g of concentrated glycerin (Glycerin content: 98 wt % or more), an appropriate amount of purified water was added to make 100 mL in total.

That is, first, a part of purified water was warmed to about at 70° C., Gosenol and concentrated glycerin were added to dissolve them and obtained an aqueous solution. Separately, latanoprost was a dissolved in Miglyol 812 to prepare an oily solution. Then, the oily solution was gradually added to the aqueous solution while being stirred with a homomixer (ROBO MICS, Tokyo Tokushu Kika. Kogyo Co., Ltd.). to perform rough emulsification (8000 rpm, 15 mm), and sterile purified water was added to the rough emulsion to make a predetermined amount of the emulsion. This rough emulsion was finely-emulsified (1500 kgf/cm$^2$, 10 pass) with a microfluidizer (M-110EH, Microfluidics Corporation) to obtain a 0.01% latanoprost emulsion (a stock liquid).

This 0.01% latanoprost emulsion was diluted about two times with the following buffers having a pH of 5, 6 or 7, respectively. The pHs of the respective emulsions were adjusted to the same pHs as those of the original buffers with NaOH and/or HCl. Thus, six kinds of emulsions of latanoprost having the final concentration of 0.005% (Formulations 1 to 6) were prepared.

Formulation 1: 0.3% ∈-aminocaproic acid buffer (pH 5)
Formulation 2: 0.2% sodium acetate buffer (pH 5)
Formulation 3: 0.2% sodium acetate buffer (pH 6)
Formulation 4: 0.2% phosphate buffer (pH 6)
Formulation 5: 0.2% phosphate buffer (pH 7)
Formulation 6: 0.2% borate buffer (pH 7)

Each 2 mL of each formulation was filled into a 2 mL brown glass ampoule, and stored at 4° C. or 60° C. for 4 weeks under light shielding. The stored sample was sampled every week, and latanoprost content was measured by a HPLC method under the same condition as that of Test Example 1. Each sample was subjected to measurement as it was without dilution. As a comparison control formation, Xalatan eye drop (trade name, containing 0.005% latanoprost. pH 6.5 to 6.9, manufactured by Pharmacia, Lot No. PT480) was stored under the same storing conditions, and latanoprost content was measured.

Test Results

Latanoprost remaining rate in each formulation:

%=(remaining amount at 60° C./remaining amount at 4° C.)×100 is shown in Table 2.

TABLE 2

| Latanoprost remaining rate (%) in formulation | | | | |
| --- | --- | --- | --- | --- |
| | 1 week | 2 weeks | 3 weeks | 4 weeks |
| Formulation 1 | 97.8 | 100.6 | 99.5 | 98.3 |
| Formulation 2 | 103.5 | 99.4 | 99.7 | 100.4 |
| Formulation 3 | 99.3 | 98.9 | 99.1 | 100.7 |
| Formulation 4 | 100.3 | 99.4 | 96.8 | 98.2 |
| Formulation 5 | 99.9 | 93.9 | 98.7 | 102.8 |
| Formulation 6 | 99.0 | 101.1 | 100.3 | 99.2 |
| Xalatan | 94.4 | 94.2 | 86.5 | 76.4 |

All latanoprost remaining rates in formulations 1 to 6 which had been stored at 60° C. for 4 weeks were higher than that of Xalatan, and it was shown that latanoprost is stable in these formulations.

As apparent from the above test results, it was recognized that an oil-in-water emulsion formulating latanoprost together with a medium chain fatty acid triglyceride and a water-soluble polymer remarkably suppressed the degradation of latanoprost.

Preparation Examples of the prostaglandin $F_{2\alpha}$ derivative-containing oil-in-water emulsion of the present invention will be shown below.

Preparation Example 1

Eye Drop

| Latanoprost | 0.01 g |
| --- | --- |
| Concentrated glycerin | 2.4 g |
| Polyvinyl alcohol | 2 g |
| Sodium acetate | 0.1 g |
| Sodium edetate | 0.01 g |
| Chlorhexidine gluconate solution (20 W/V %) | 0.025 mL |
| Miglyol 812 | 1 g |
| Hydrochloric acid | q.s. |
| Purified water | ad 100 mL |
| pH | 7.0 |

According to the above formulation, concentrated glycerin and polyvinyl alcohol were dispersed in an aqueous sodium acetate solution, the dispersion was warmed and dissolved while vigorously stirring with a homomixer, and Miglyol in which latanoprost had been dissolved was added to prepare an emulsion. The emulsion was cooled to room temperature, sodium edetate, and a chlorhexidine gluconate solution were added, 1 N hydrochloric acid was added to adjust a pH. After the addition of purified water to make a predetermined volume, the emulsion was sterilized by filtration to prepare an eye drop.

Preparation Example 2

Eye Drop

| Latanoprost | 0.005 g |
| --- | --- |
| Concentrated glycerin | 2.4 g |
| Boric acid | 1.6 g |
| Sodium edetate | 0.01 g |
| Sorbic acid | 0.2 g |
| Hydroxypropylmethylcellulose | 0.9 g |
| Miglyol 812 | 0.6 g |
| Hydrochloric acid | q.s. |
| Purified water | ad 100 mL |
| pH | 7.0 |

According to the above formulation, concentrated glycerin and hydroxypropylmethylcellulose were gradually dispersed in an aqueous boric acid solution, the dispersion was warmed and dissolved while vigorously stirring with a homomixer, and Miglyol in which latanoprost had been dissolved was further added to prepare an emulsion. The emulsion was cooled to room temperature, sodium edetate and sorbic acid were added, hydrochloric acid was added to adjust a pH. After the addition of purified water to make a predetermined volume, the emulsion was sterilized by filtration to prepare an eye drop.

Preparation Example 3

Eye Drop

| Latanoprost | 0.005 g |
| --- | --- |
| Concentrated glycerin | 2.4 g |
| Sodium acetate | 0.1 g |
| Sodium edetate | 0.01 g |
| Sorbic acid | 0.2 g |
| Xanthan gum | 0.9 g |
| Peanut oil | 0.6 g |
| Hydrochloric acid | q.s. |
| Purified water | ad 100 mL |
| pH | 6.0 |

According to the above formulation, concentrated glycerin and xanthan gum were gradually dispersed in an aqueous sodium acetate solution, the dispersion was warmed and dissolved while vigorously stirring with a homomixer, and a peanut oil in which latanoprost had been dissolved was further added to prepare an emulsion. The emulsion was cooled to room temperature, sodium edetate and sorbic acid were added, 1 N hydrochloric acid was added to adjust a pH. After the addition of purified water to make a predetermined volume, the emulsion was sterilized by filtration to prepare an eye drop.

Preparation Example 4

| Isopropyl unoprostone | 0.12 g |
| --- | --- |
| Concentrated glycerin | 2.4 g |
| Polyvinyl alcohol | 2.0 g |
| Sodium acetate | 0.1 g |
| Sodium edetate | 0.01 g |

| | |
|---|---|
| Chlorhexidine gluconate solution 20 (W/V %) | 0.025 mL |
| Miglyol 812 | 1.0 g |
| Hydrochloric acid | q.s. |
| Purified water | ad 100 mL |
| pH | 6.0 |

According to the above formulation, concentrated glycerin and polyvinyl alcohol were dispersed in an aqueous sodium acetate solution, the dispersion was warmed and dissolved while vigorously stirring with a homomixer. Miglyol in which isopropyl unoprostone had been dissolved was further added to prepare an emulsion. The emulsion was cooled to room temperature, and sodium edetate, and a chlorhexidine gluconate solution were added. 1 N hydrochloric acid was added to adjust a pH and purified water was added to make a predetermined volume, the emulsion was sterilized by filtration to prepare an eye drop.

Preparation Example 5

| | |
|---|---|
| Isopropylunoprostone | 0.12 g |
| Concentrated glycerin | 2.4 g |
| Polyvinyl alcohol | 2.0 g |
| Polysorbate 80 | 2.0 g |
| Sodium acetate | 0.1 g |
| Sodium edetate | 0.01 g |
| Sorbic acid | 0.2 g |
| Miglyol 812 | 5.0 g |
| Hydrochloric acid | q.s. |
| Purified water | ad. 100 mL |
| PH | 6.5 |

According to the above formulation, concentrated glycerin, Polysorbate 80 and polyvinyl alcohol were dispersed in an aqueous sodium acetate solution, and the dispersion was warmed and dissolved while vigorously stirring with a homomixer. Isopropyl unoprostone dissolved in Miglyol was further added to prepare an emulsion. The emulsion was cooled to room temperature, and sodium edetate and sorbie acid were added. IN hydrochloric acid was added to adjust a pH, and the emulsion was measured up, and sterilized by filtration to prepare an eye drop.

Industrial Applicability

The present invention can provide a stable pharmaceutical composition containing a prostaglandin $F_{2\alpha}$ derivative, for example, an eye drop which is applied to glaucoma or high ocular tension.

The invention claimed is:

1. A method for suppressing degradation of a prostaglandin $F_{2\alpha}$ derivative selected from the group consisting of latanoprost, isopropyl unoprostone, travoprost and bimatoprost in an oil-in-water emulsion ophthalmological composition, which comprises:

dissolving the prostaglandin $F_{2\alpha}$ derivative in a medium chain fatty acid triglyceride to obtain an oily solution, and adding the oily solution to a mixture comprising water and a water-soluble polymer selected from the group consisting of a water-soluble polyvinyl compound, a water-soluble cellulose compound and a water-soluble polysaccharide to obtain the oil-in-water emulsion ophthalmological composition, thereby suppressing the degradation of the prostaglandin $F_{2\alpha}$ derivative.

2. The method according to claim 1, wherein the prostaglandin $F_{2\alpha}$ derivative is latanoprost.

3. The method according to claim 1, wherein the water-soluble polymer is polyvinyl alcohol.

4. The method according to claim 1, wherein the oil-in-water emulsion ophthalmological composition is an eye drop.

5. The method according to claim 1, wherein the oil-in-water emulsion ophthalmological composition is an eye drop comprising latanoprost, an oil comprising caprylic acid, polyvinyl alcohol and water.

6. The method according to claim 1, wherein the oil-in-water emulsion ophthalmological composition comprises:
0.0001 to 0.4 (W/V) % of the prostaglandin $F_{2\alpha}$ derivative;
0.005 to 20 (W/V) % of the medium chain fatty acid triglyceride; and
0.001 to 20 (W/V) % of the water-soluble polymer.

* * * * *